US00PP15744P2

(12) United States Plant Patent
Dirr

(10) Patent No.: US PP15,744 P2
(45) Date of Patent: May 3, 2005

(54) ***HYDRANGEA MACROPHYLLA* PLANT NAMED 'MINI PENNY'**

(50) Latin Name: *Hydrangea macrophylla*
Varietal Denomination: Mini Penny

(75) Inventor: Michael A. Dirr, Watkinsville, GA (US)

(73) Assignee: University of Georgia Research Foundation, Inc., Atlanta, GA (US)

( * ) Notice: Subject to any disclaimer, the term of this patent is extended or adjusted under 35 U.S.C. 154(b) by 0 days.

(21) Appl. No.: 10/738,671

(22) Filed: Dec. 17, 2003

(51) Int. Cl.[7] ..... A01H 5/00
(52) U.S. Cl. ..... Plt./250
(58) Field of Search ..... Plt./250

*Primary Examiner*—Kent Bell
(74) *Attorney, Agent, or Firm*—MacCord Mason PLLC

(57) ABSTRACT

*Hydrangea macrophylla* 'Mini Penny' is a mophead with compact, mounded habit, leathery, lustrous dark green, mildew resistant leaves, which reblooms on new growth without the need for cool temperatures and short days.

4 Drawing Sheets

Botanical designation: *Hydrangea macrophylla* plant named 'Mini Penny'.

Latin name of the genus and species of the plant claimed: *Hydrangea macrophylla.*

Variety denomination: Mini Penny.

BACKGROUND OF THE INVENTION

1. Field of the Invention

The present invention relates to a new and distinct variety of *Hydrangea macrophylla* (Thunb.) Ser., a member of the Hydrangeaceae family. *Hydrangea macrophylla* 'Mini Penny' is the result of a controlled breeding program in Athens, Ga. The variety originated from open-pollinated *Hydrangea macrophylla* 'Penny Mac' (unpatented), and a single plant was selected from a seedling population after evaluation. The plant is used primarily as an ornamental.

The variety, 'Mini Penny', reproduces true to type in successive generations of asexual reproduction from shoot cuttings.

2. Description of Relevant Prior Art

'Mini Penny' is distinguished from its parent *Hydrangea macrophylla* 'Penny Mac' and all other varieties of *Hydrangea macrophylla* known to the inventor by the combination of its characters, tidy, refined, broad-mounded compact habit, smaller than typical, leathery, lustrous dark green, mildew-resistant leaves, and ability to flower on new growth (remontant).

SUMMARY OF THE INVENTION

*Hydrangea macrophylla* 'Mini Penny' develops a compact habit and leathery, lustrous dark green, mildew-resistant leaves. The pink or blue mophead flowers develop on new growth and flower without the cool temperatures and short days that are required for floral induction in the traditional varieties. On Jun. 25, 2002, 33 fully developed inflorescences were removed from a 2-year-old plant, and by Oct. 4, 2002, there were 34 visible flower buds or fully developed inflorescences.

BRIEF DESCRIPTION OF ILLUSTRATIONS

The accompanying illustrations show characteristics of the new cultivar in photographs as true to color as is reasonably possible to make in illustrations of this nature.

BOTANICAL DESCRIPTION OF THE PLANT

Figure 1:
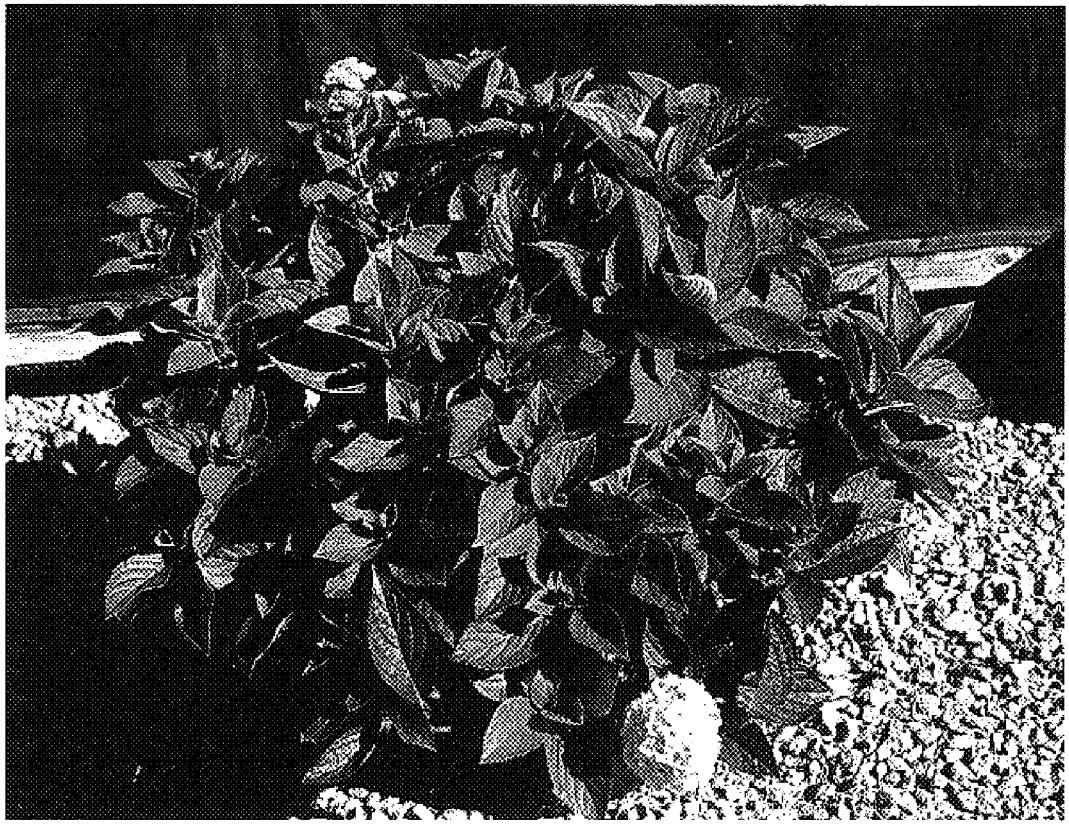
FIG. 1 shows a 2-year-old unpruned plant in a 27 liter container
Figure 2:
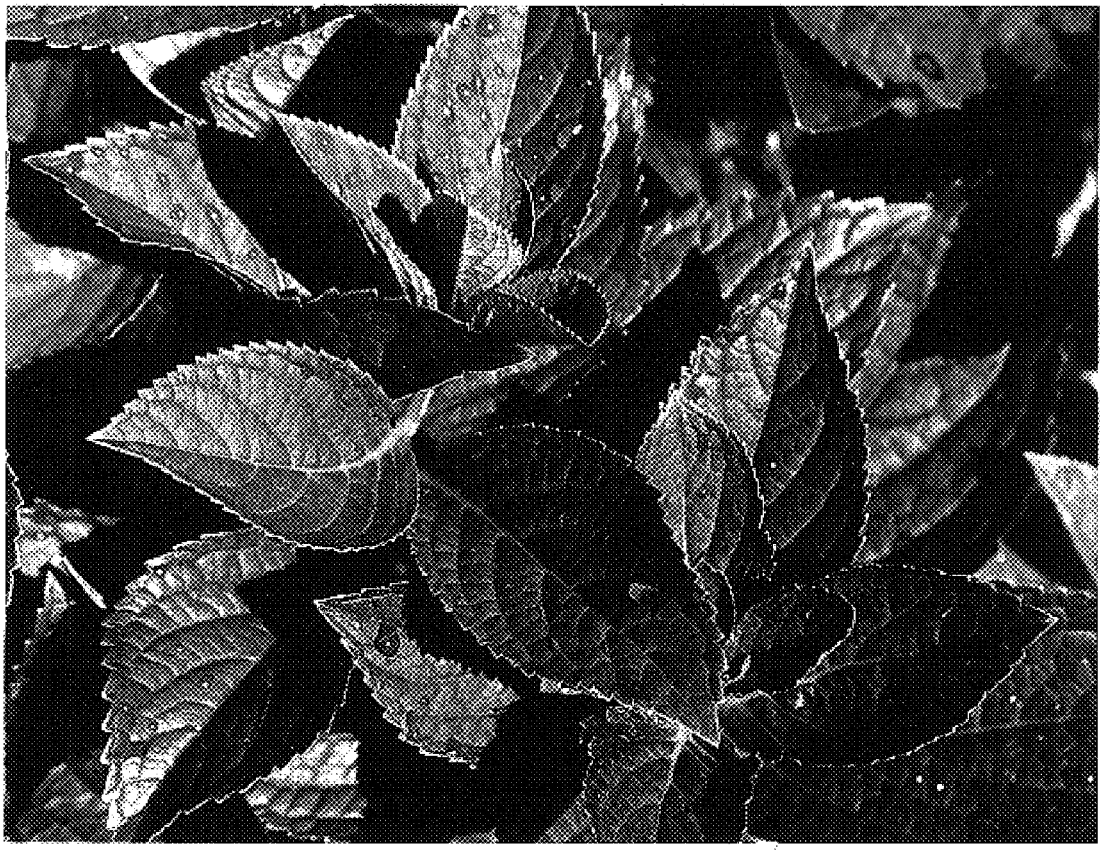
FIG. 2 illustrates the summer leaf color and texture
Figure 3:
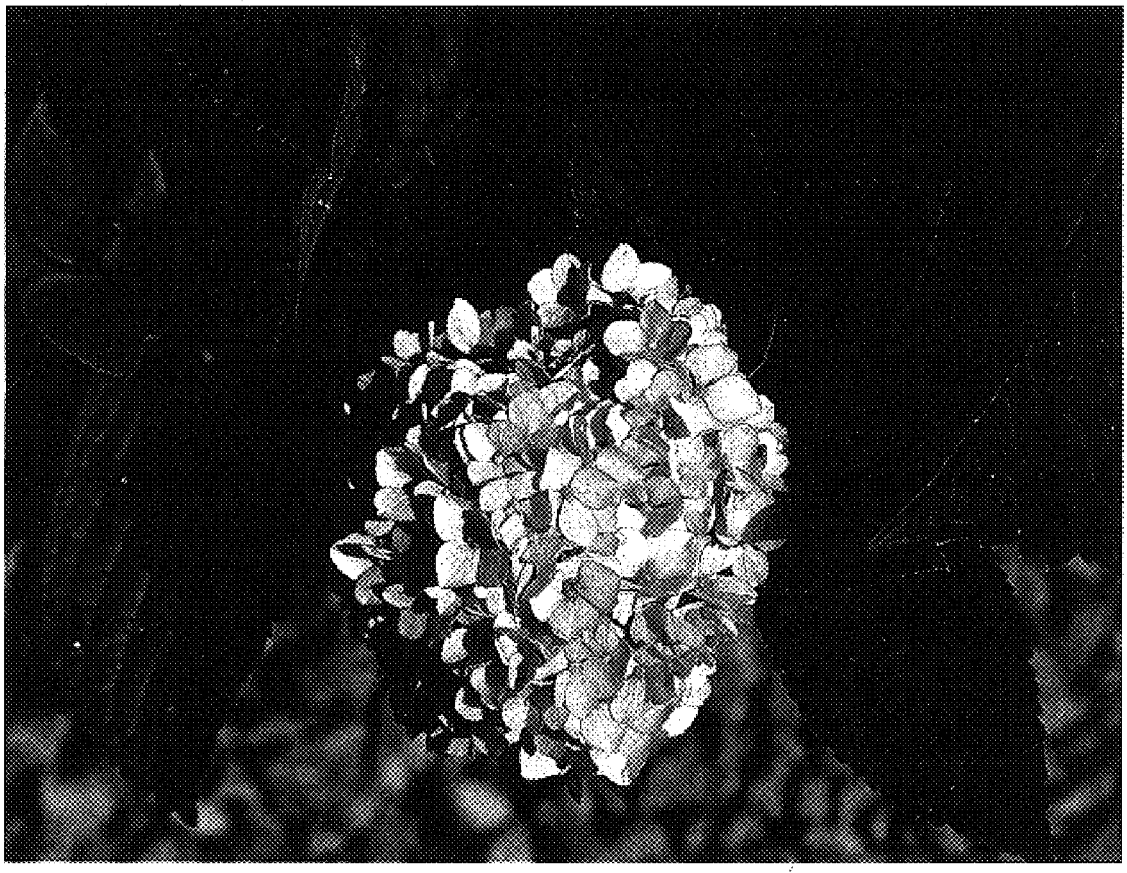
FIG. 3 illustrates a mature inflorescence (no aluminum present).
Figure 4:
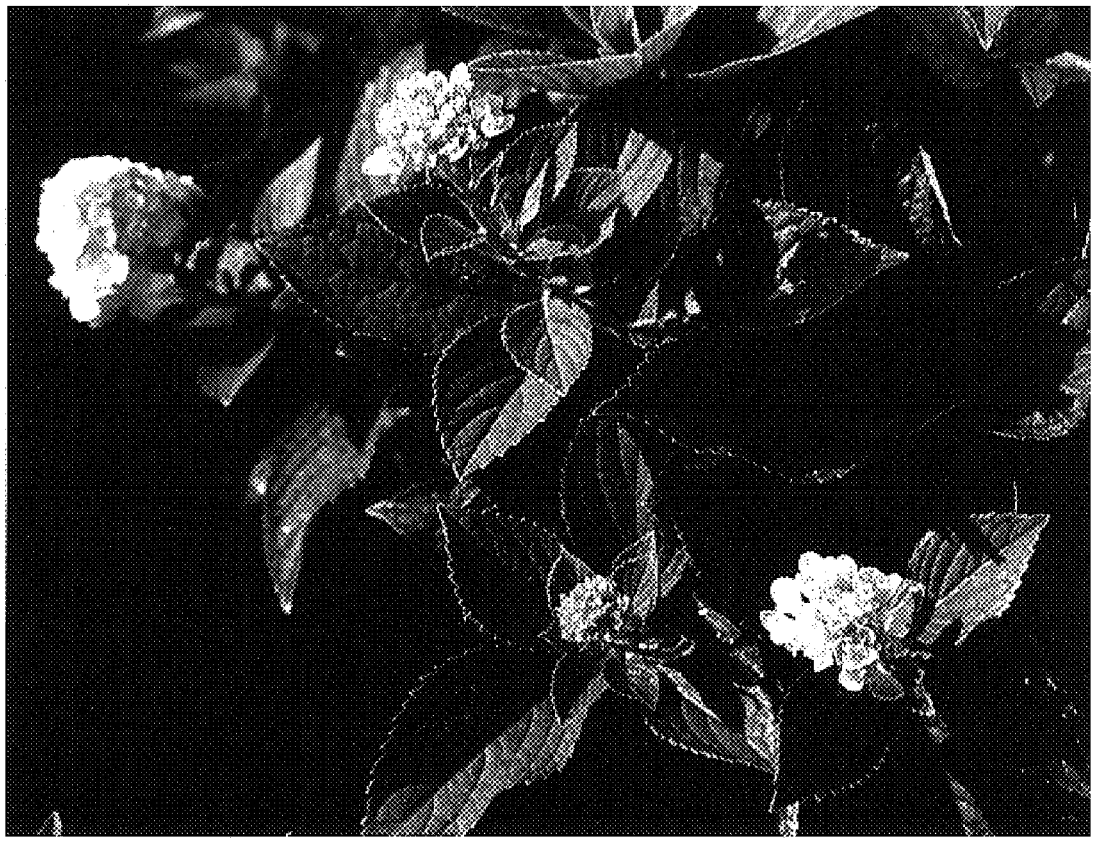
FIG. 4 illustrates new flower buds and inflorescences developing on Oct. 4, 2002, after all inflorescences were removed on Jun. 25, 2002.

A detailed description of *Hydrangea macrophylla* 'Mini Penny' follows. Colors are based on The Royal Horticultural Color Chart (1995). All measurements/characteristics were taken from a 2-year-old plant in a 27 liter nursery container grown out of doors under 50% shade at Dearing, Ga. (USDA zone 7.b). Plants grown outside flag under full sun, and 30% to 50% shade is recommended. Measurements of leaves/stems and floral characteristics are based on 10 to 20 samples.

Classification:

*Botanical.*—*Hydrangea macrophylla* (Thunb.) Ser. 'Mini Penny'.

*Parentage.*—Open-pollinated seedling of *Hydrangea macrophylla* 'Penny Mac'.

*Propagation.*—Vegetatively by cuttings.

Plant:

*Size.*—On average 41 cm high, 91 cm wide in 2 years.

*Habit.*—Mounded deciduous shrub, multistemmed and extremely compact.

*Branching.*—Many breaks (shoots) from base of one-year plants, ie, freely branching. The plant is highly resistant to insects and diseases, including mildew.

Leaf:

*Shape.*—Ovate.

*Base.*—Cuneate.

*Apex.*—Acute.

*Size.*—Length 13.9 cm, width 7.7 cm.

*Arrangement.*—Opposite.

*Margin.*—Coarsely serrate.

*Texture/substance.*—Thickish; glabrous on upper and lower surfaces; 6 to 8 prominent raised vein pairs on lower surface.

*Petioles.*—1.40 cm long, glabrous, grooved above, rounded below. Color: Yellow-Green Group 145A.

*Mature leaf color.*—Summer color varies with nutrition and intensity of sunlight. Upper leaf surface typically Yellow-Green Group 147A; lower surface Green Group 137C. Lower leaf surface veins are Yellow-Green Group 145A.

Stems:

*Length.*—Stems varied in length from 17 to 48 cm, with an average length of 30 cm.

*Thickness.*—0.4 cm.

*Texture.*—Slender, terete, glabrous, lustrous.

*Internode length.*—2.8 cm.

*Color.*—Yellow-Green group 145A.

*Hardiness.*—USDA (1990) Zone 7 (−17.8° C. to −12.2° C.) to 9 (−6.7° C. to −1.1° C.).

*Vigor.*—Slow, 2-year old plants range from 38 to 51 cm tall by 76 to 102 cm wide.

Inflorescence:

*Bloom period.*—May to November, Athens and Dearing, Ga.

*Flower arrangement.*—Corymb, mophead, with sterile florets (sepals) covering the fertile flowers in the interior.

*Shape of inflorescence.*—Rounded.

*Inflorescence size.*—9 to 11 cm diameter with the average depth of 6 cm. The number of fertile flowers per inflorescence varies from 16 to 18.

*Floral buds.*—Immature buds are round, 3 mm long by 3 mm wide by 2 mm deep, and are Yellow-Green Group 145D. Mature buds are round, 4 mm long by 4 mm wide by 3 mm deep and are Purple Group 75C.

*Peduncle.*—Range in length from 10 mm to 15 mm and approximately 1 mm in diameter. Color is Red-Purple Group 62B.

*Pedicil.*—The pedicil of the fertile flower has an average length of 2 mm with 1 mm diameter, and are Greyed-Purple Group 185D. The pedicils of the sterile florets vary in length from 5 mm to 15 mm with 1 mm diameter, and are Red Group 65C.

*Fertile flowers.*—Insignificant and hidden by sterile florets. The immature fertile flowers are Yellow-Green Group 145B, with five stamens and five petals. The mature petals are elliptical and cupped, 3 mm long and 2 mm wide. The color of the upper surface of the mature petals is Purple Group 77C and the lower surface is Purple Group 76C.

*Sterile florets.*—Four sepals per cluster (showy floret), 2.45 cm diameter; each sepal —glabrous, apex acute to rounded, sometimes notched, base rounded, rounded in outline, entire, 1.5 cm long, 1.4 cm wide.

*Color.*—Sterile florets on plants not treated with aluminum sulfate: Upper surface Red-Purple Group 73D grading to Red-Purple Group 72C at base of sepals, lower surface Purple Group 75B to Purple Group 75C to Purple Group 75D. Sterile florets on plants treated with aluminum sulfate (42 grams per 3.8 liters of $H_2O$ applied as soil drench when flower buds were visible) Violet-Blue Group 95C grading to White Group 155D at base of sepals on upper surface and Violet-Blue Group 94C to Violet-Blue Group 97A on the lower surface.

*Fragrance.*—None noted.

*Persistence of inflorescence.*—2 to 3 months.

Reproductive system:

*Fertile flowers.*—One pistil with 3, occasionally 4, stigmas, and 5 stamens on fertile flowers; pollen: white.

*Fruit.*—Fertile capsule, urn-shaped, 0.5 cm long, 0.3 cm wide, Brown Group 200B. Each capsule contains 50 to 200 sheets which are approximately 0.5 mm long by 0.25 mm wide, with color Greyed-Orange Group 164C.

It is claimed:

1. A new and distinct variety of *Hydrangea macrophylla* plant, substantially as herein described and illustrated.

* * * * *